US010408846B2

(12) United States Patent  
Gustavson et al.

(10) Patent No.: US 10,408,846 B2  
(45) Date of Patent: Sep. 10, 2019

(54) QUANTITATIVE METHODS AND KITS FOR PROVIDING REPRODUCIBLE IHC4 SCORES

(71) Applicant: Novartis AG, Basel (CH)

(72) Inventors: Mark D. Gustavson, Greensboro, NC (US); Jason Christiansen, Carlsbad, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/841,887

(22) Filed: Mar. 15, 2013

(65) Prior Publication Data

US 2013/0310267 A1    Nov. 21, 2013

Related U.S. Application Data

(60) Provisional application No. 61/647,371, filed on May 15, 2012.

(51) Int. Cl.
| | |
|---|---|
| *G01N 33/48* | (2006.01) |
| *G01N 33/68* | (2006.01) |
| *G01N 33/574* | (2006.01) |
| *G01N 33/74* | (2006.01) |

(52) U.S. Cl.  
CPC ....... *G01N 33/6893* (2013.01); *G01N 33/574* (2013.01); *G01N 33/57415* (2013.01); *G01N 33/57484* (2013.01); *G01N 33/74* (2013.01); *G01N 33/743* (2013.01); *G01N 2800/50* (2013.01); *G01N 2800/54* (2013.01)

(58) Field of Classification Search  
None  
See application file for complete search history.

(56) References Cited

U.S. PATENT DOCUMENTS

2012/0003639 A1    1/2012    Kerlikowske et al.

FOREIGN PATENT DOCUMENTS

| WO | WO-2005/008213 A2 | 1/2005 |
| WO | WO-2006/119593 A1 | 11/2006 |

OTHER PUBLICATIONS

Cuzick et al. Journal of Clinical Oncology 29.32 (2011): 4273-4278.*  
Cuzick et al. Cancer Res 69.24 Suppl (2009): 74.*  
Dowsett et al.Journal of Clinical Oncology 28.11 (2010): 1829-1834.*  
Harigopal et al. ( The American journal of pathology 176.4 (2010): 1639-1647).*

(Continued)

*Primary Examiner* — Larry D Riggs, II  
(74) *Attorney, Agent, or Firm* — Gilberto M. Villacorta; Foley & Lardner LLP

(57) ABSTRACT

The present technology relates generally to determining a risk of recurrence of disease in a cancer patient. In particular, this approach to determining a risk of recurrence involves utilizing standardized quantitative assessments of the level of biomarker expression selected from estrogen receptor (ER), progesterone receptor (PR), human epidermal growth factor receptor 2 (HER2) and Ki-67 (Ki67) in a patient's tumor to determine the risk of recurrence, thereby allowing a caretaker to determine the best course of treatment for the patient.

21 Claims, 5 Drawing Sheets

(56) References Cited

OTHER PUBLICATIONS

Cuzick, J. et al., "Prognostic Value of a Combined ER, PgR, Ki67, HER2 Immunohistochemical (IHC4) Score and Comparison with the GHI Recurrence Score—Results from TransATAC," Cancer Research, [Online], vol. 69, No. 24, Suppl. 3, Dec. 15, 2009, 2 pgs.
Cuzick, J. et al., "Prognostic Value of a Combined Estrogen Receptor, Progesterone Receptor, Ki-67, and Human Epidermal Growth Factor Receptor 2 Immunohistochemical Score and Comparison with the Genomic Health Recurrence Score in Early Breast Cancer," Journal of Clinical Oncology, vol. 29, No. 32, Nov. 10, 2011, pp. 4273-4278.
Gustavson, M. et al., "Development of an Unsupervised Pixel-based Clustering Algorithm for Compartmentalization of Immunohistochemical Expression Using Automated Quantitative Analysis," Applied Immunohistochemistry, vol. 17, No. 4, Jul. 1, 2009, pp. 329-337.
International Search Report and Written Opinion dated Oct. 15, 2013 in PCT/US2013/040874.
Paik, et al. "A Multigene Assay to Predict Recurrence of Tamoxifen-Treated Node-Negative Breast Cancer", N. Engl. J. Med. (2004), vol. 351, pp. 2817-2826.

\* cited by examiner

QUANTITATIVE METHODS AND KITS FOR PROVIDING REPRODUCIBLE IHC4 SCORES

CROSS-REFERENCE TO RELATED PATENT APPLICATIONS

This application claims the benefit of the priority date of U.S. Provisional Application Ser. No. 61/647,371, filed May 15, 2012, the content of which is incorporated herein by reference in its entirety.

FIELD OF THE INVENTION

The present technology relates generally to determining a risk of recurrence of disease in a cancer patient. In particular, this approach to determining a risk of recurrence involves utilizing standardized quantitative assessments of the level of biomarker expression selected from estrogen receptor (ER), progesterone receptor (PR), human epidermal growth factor receptor 2 (HER2) and Ki-67 (Ki67) in a patient's tumor to determine the risk of recurrence, thereby allowing a caretaker to determine the best course of treatment for the patient.

BACKGROUND OF THE INVENTION

The following discussion of the background is merely provided to aid the reader in understanding the technology and is not admitted to describe or constitute prior art to the present application.

Cancer treatment in patients can take on many forms. A patient may be subjected to treatment regimens, including but not limited to radiation therapy, surgery, chemotherapy, hormonal or endocrine therapy, or combinations thereof. One of many considerations that a treating physician may take into account is the relative risk of recurrence when proposing a planned course of treatment. For example, in estrogen receptor (ER) positive breast cancer patients, the current treatment is predominantly hormonal therapy, such as Tamoxifen or Aromatase inhibitors, which have been shown to reduce recurrence and mortality. However, for ER positive patients treated with 5 years of adjuvant hormonal therapy, more than 50% of recurrences arise after 5 years and recurrence risk prevails through 20+ years. In order to prevent recurrence, physicians will commonly prescribe chemotherapy in addition to hormonal therapy. However, not all patients benefit from the additional chemotherapy, and prognostic methods are needed to quantify the recurrence risk.

Several methods have been developed to attempt to quantify the risk of recurrence. See, e.g., Paik et al., *A Multigene Assay to Predict Recurrence of Tamoxifen-Treated, Node-Negative Breast Cancer*, N. Engl. J. Med.; 351:2817-2826, 2004, which is hereby incorporated by reference in its entirety. However, these tests suffer from high cost, limited access as the assay must be carried out in a central laboratory and require large specimen samples.

Additional tests, such as the immunohistochemical score "IHC4" have been developed, which combine the biomarkers estrogen receptor (ER), progesterone receptor (PR), human epidermal growth factor receptor 2 (HER2) and Ki-67 (Ki67) ("Cuzick model"). See Cuzick, et al., Cancer Res. 2009; 69(Suppl): Abstract 74; Cuzick et al., *Prognostic value of a Combined Estrogen Receptor, Progesterone Receptor, Ki-67, and Human Epidermal Growth Factor Receptor 2 Immunohistochemical Score and Comparison With the Genomic Health Recurrence Score in Early Breast Cancer*, J. Clin. Oncol. 2011; 29: 4273-4278. However, the IHC4 Risk Score provided for in these publications was determined by one laboratory, and is prone to a general lack of reproducibility, thereby rendering it unsuitable for widespread use.

Thus, there is a need for a reproducible, relatively inexpensive test for determining the recurrence risk for patients suffering from cancer, for example breast cancer.

SUMMARY OF THE INVENTION

The present technology is based on the discovery of that a patient's risk of recurrence of cancer can be more accurately predicted by determining a cumulative score based on a score model in which the continuous, quantitative scores provided the level of expression of each of at least three of the following four biomarkers, including estrogen receptor (ER), progesterone receptor (PR), human epidermal growth factor receptor 2 (HER2) and Ki-67 (Ki67). Provided herein are methods and kits for determining the risk of recurrence of cancer, for example breast cancer, in patients suffering therefrom. In some embodiments, the technique used in the method of the invention includes an objective, reproducible, quantitative, multiparametric analysis of the level of expression of each of said four biomarkers.

In one aspect, the present invention provides a method of determining a risk of recurrence of disease in a cancer patient—in some embodiments, a breast cancer patient—comprising: determining a level of expression of each of at least three of the following four biomarkers, including estrogen receptor (ER), progesterone receptor (PR), human epidermal growth factor receptor 2 (HER2) and Ki-67 (Ki67), in a tumor specimen taken from a cancer patient, the determination utilizing a technique that provides a continuous, quantitative score of the level of expression of each of the at least three of said four biomarkers; determining a cumulative score based on a score model in which the continuous, quantitative scores provided by the technique, one each for the at least three of said four biomarkers, are incorporated; and determining a risk of recurrence of disease in the cancer patient based on the cumulative score. In some embodiments, the method further comprises prescribing an aggressive treatment regimen to a patient determined to be at a high risk of recurrence of disease and/or subjecting a patient determined to be at a high risk of recurrence of disease to radiation therapy or chemotherapy. In one embodiment, the continuous, quantitative score is intensity-based. In another embodiment, the continuous, quantitative score is both intensity-based and area-based. In yet another embodiment, the continuous, quantitative score is determined for each of said four biomarkers and applied to a cumulative score. Another embodiment includes the recited method in which increasing cumulative scores indicate increasing risk of recurrence of disease. In some embodiments, the cancer patient has been diagnosed with breast cancer, which may be ER and/or PR positive. In some embodiments, the cancer patient has undergone anti-estrogen hormonal treatment. In other embodiments, the cancer patient has yet to undergo treatment for the patient's cancer. The cancer patient, in some embodiments, is assigned to a quartile, based on the cumulative recurrence score, a first quartile representing cancer patients having lowest cumulative scores and lowest risk of recurrence of disease and a fourth quartile representing cancer patients having highest cumulative scores and highest risk of recurrence of disease. A cancer patient assigned to the fourth quartile may be considered a candidate for an aggressive treatment regimen, including chemotherapy, radiation therapy, or a combination thereof, and a cancer patient assigned to the first quartile may be considered a candidate who would not be expected to benefit from an aggressive treatment regimen, including chemotherapy, radiation therapy, or a combination thereof. Additionally, the cancer patient assigned to intermediate quartiles may be considered a candidate with intermediate risk, and may benefit from additional treatment or supervision. In some embodiments, the technique includes an automated, quantitative image analysis procedure, optionally implemented by an automated, digital pathology system. In another embodiment, the automated, quantitative image analysis procedure is implemented by an automated, digital, immunofluorescence pathology system. In other embodiments, the technique includes an automated, quantitative, immunofluorescence image analysis procedure. In some embodiments, the score model that provides the cumulative score (IHC4$_{cs}$) comprises an algorithm (I), which is:

$$IHC4_{cs}=94.7*[0.100ER_{10}-0.079PR_{10}+0.586HER2+ 0.240\ln(1+10*Ki67)] \quad (I)$$

in which $ER_{10}$ represents the normalized, continuous, quantitative score of the level of expression of ER; $PR_{10}$ represents the normalized continuous, quantitative score of the level of expression of PR; HER2 represents the dichotomized score derived from, continuous, quantitative scores for the level of expression of HER2; and Ki67 represents the percent positive, score of Ki67. In other embodiments, the score model that provides the cumulative score (IHC4$_{cs}$) comprises an algorithm (II), which is:

$$IHC4_{cs}=(-0.152*ER)-(0.007*PR)+(0.001*HER2)+ (0.082*Ki67) \quad (II)$$

in which ER represents the continuous, quantitative score of the level of expression of ER; PR represents the continuous, quantitative score of the level of expression of PR; HER2 represents the continuous, quantitative score of the level of expression of HER2; and Ki67 represents the continuous, quantitative score of the level of expression of Ki67.

In another aspect, the present invention provides a method of determining a risk of recurrence of disease in a cancer patient—in some embodiments, a breast cancer patient—comprising: determining a level of expression of each of four biomarkers, including estrogen receptor (ER), progesterone receptor (PR), human epidermal growth factor receptor 2 (HER2) and Ki-67 (Ki67), in a tumor specimen taken from a cancer patient, the determination utilizing a technique that provides a continuous, quantitative score of the level of expression of each of said four biomarkers; determining a cumulative score based on a score model comprising an algorithm (III), which is:

$$IHC4_{cs}=(-0.151*ER)-(0.207*PR)+(0.217*HER2)+ (0.077*Ki67) \quad (III)$$

in which ER represents the continuous, quantitative score of the level of expression of ER; PR represents the continuous, quantitative score of the level of expression of PR; HER2 represents the dichotomous score, derived from the continuous, quantitative score of the level of expression of HER2; and Ki67 represents the continuous, quantitative score of the level of expression of Ki67.

In another aspect, the present invention provides an assay kit for determining a risk of recurrence of disease in a cancer patient comprising reagents for determining a continuous, quantitative score of a level of expression, if desired, of each of four biomarkers, including estrogen receptor (ER), progesterone receptor (PR), human epidermal growth factor receptor 2 (HER2) and Ki-67 (Ki67), in a tumor specimen taken from a cancer patient. In some embodiments, the assay kit includes instructions for the use of said reagents. In another embodiment, the assay kit includes at least the following reagents: a first stain specific for a nuclear compartment of a cell; a second stain specific for estrogen receptor (ER); a third stain specific for progesterone receptor (PR); a fourth stain specific for human epidermal growth factor receptor 2 (HER2); a fifth stain specific for Ki-67; and a sixth stain specific for epithelial cytoplasmic subcellular compartment.

In another aspect, the present invention provides a computer system, including one or more excitation light sources, optical components, image capture components, storage components and one or more processors, configured to execute a computer program comprising computer-readable instructions for determining a continuous, quantitative score of a level of expression of each of at least three of the following four biomarkers, including estrogen receptor (ER), progesterone receptor (PR), human epidermal growth factor receptor 2 (HER2) and Ki-67 (Ki67), in a tumor specimen taken from a cancer patient;

In another aspect, the present invention provides a non-transitory computer-usable medium having computer-readable instructions stored thereon for execution by a processor to perform a method for determining a continuous, quantitative score of a level of expression of each of at least three of the following four biomarkers, including estrogen receptor (ER), progesterone receptor (PR), human epidermal growth factor receptor 2 (HER2) and Ki-67 (Ki67), in a tumor specimen taken from a cancer patient; determining a cumulative score based on a score model that incorporates said at least three continuous, quantitative scores; and determining a risk of recurrence of disease in the cancer patient based on the cumulative score.

In another aspect, the present invention provides a non-transitory computer-usable medium having program code recorded thereon that, when executed on a computing system, automatically processes immunofluorescence data, the program code comprising: code for processing a digital microscopy image of a stained tumor specimen taken from a cancer patient to extract data related to intensity values associated with one or more stains; code for processing the extracted data to arrive at a value for intensity per pixel for each of the one or more stains; code for processing pixel intensity of at least one stain for determining pixels associated with a preselected subcompartment and determining the area of the subcompartment for use as a denominator; code for processing pixel intensity of a second stain for determining an expression level of a biomarker on a continuous scale and a value for total biomarker intensity in the same preselected subcompartment for use as a numerator; code for calculating from the numerator and denominator a quantitative score of the biomarker expression per area; optionally, code for processing the total area (pixels) stained by Ki67 as the numerator; optionally, code for total tumor nuclear compartment area as the denominator; code for collecting the quantitative score of each of at least three of the following four biomarkers, including estrogen receptor (ER), progesterone receptor (PR), human epidermal growth factor receptor 2 (HER2) and Ki-67 (Ki67); and optionally code for incorporating the continuous, quantitative scores of the at least three biomarkers into a score model for arriving at a cumulative score. In another embodiment, program code can also comprise code for determining a risk of recurrence of disease in the cancer patient based on the cumulative score; code for assigning the cumulative score to first, second, third, or fourth quartile; and/or code for determining a risk of recurrence of disease in the cancer patient based on the cumulative score by designating the position of the cumulative score of the patient on a curve of possible scores from a population of patients.

In another aspect, the present invention provides a method of determining a risk of recurrence score in a cancer patient comprising: determining a level of expression of each of at least three of the following four biomarkers, including estrogen receptor (ER), progesterone receptor (PR), human epidermal growth factor receptor 2 (HER2) and Ki-67 (Ki67), in a tumor specimen taken from a cancer patient, the determination utilizing a technique that provides a continuous, quantitative score of the level of expression of each of the at least three of said four biomarkers; determining a cumulative score based on a score model in which the continuous, quantitative scores provided by the technique, one each for the at least three of said four biomarkers, are incorporated.

In some embodiments the continuous, quantitative score is intensity-based, or both intensity-based and area-based. In other embodiments, the continuous, quantitative score is determined for each of said four biomarkers. The technique, in an embodiment, includes an automated, quantitative image analysis procedure or the technique includes an automated, quantitative, immunofluorescence image analysis procedure, and the automated, quantitative image analysis procedure may be implemented by an automated, digital pathology system or a immunofluorescence pathology system.

As used herein, "AQUA" technology refers to a fluorescence-based platform enabling objective and completely standardized quantification of protein expression in tissue with minimized operator interaction that provides tumor-specific, quantitative and continuous expression score data. AQUA technology is described in detail in U.S. Pat. Nos. 7,219,016; 8,063,833; 8,121,794; 8,185,320 and published US Patent Application Nos. US2009/0034823 and US2010/136549 the disclosures of which are hereby incorporated in their entirety by reference herein.

As used herein, "patient" refers to a human that has been diagnosed with a cancer or as having an increased likelihood of developing a cancer. A patient may be subjected to treatment regimens, including but not limited to radiation therapy, surgery, chemotherapy, hormonal or endocrine therapy, or combinations thereof.

As used herein, a "cohort" refers to a group of subjects or specimens that share certain defining characteristics, for example, tissue type (e.g., tumor sample), tamoxifen treatment status, and/or ER-positive status.

As used herein, a "computer-assisted method" refers to any immunohistochemistry analysis with at least one step, e.g., steps comprising quantitative analysis, performed or regulated by a computer or other programmable machine that inputs, stores, or manipulates data, or provides output in a useful format.

As used herein, "tumor sample" refers to an invasive breast cancer specimen from a patient that consists essentially of a population of tumor cells. In a preferred embodiment, biomarker expression in the tumor sample is specifically quantified in tumor cells (e.g., AQUA analysis) or, in another preferred embodiment, the a quantitative biomarker analysis is conducted specifically on the tumor component of the sample and not stroma and other nontumor components that may be present in surrounding connective tissue. That is, a tumor sample should be obtained and prepared or otherwise examined such that a quantitative analysis of the level of biomarker expression can be attributed substantially, if not solely, to biomarker expression in tumor cells.

DETAILED DESCRIPTION

Figure 1:
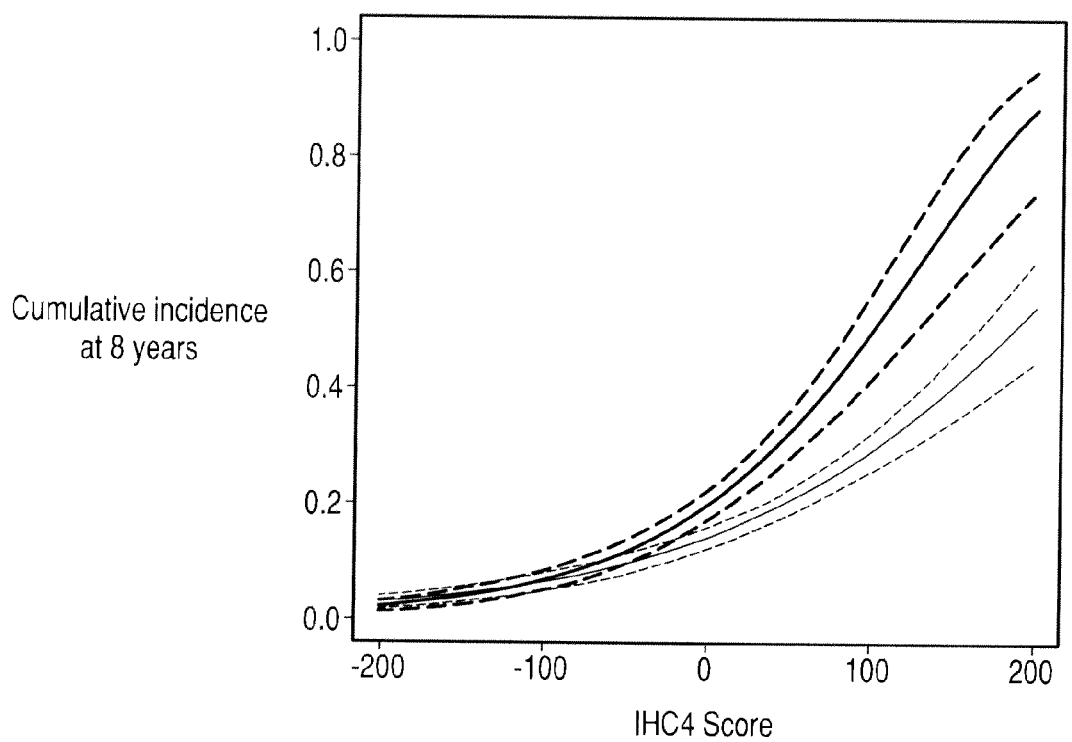
FIG. 1 illustrates an embodiment of the Hazard ratio and recurrence rate comparisons for DAB-IHC and QIF-AQUA scoring models. Cubic-spline regression plot showing the continuous relationship between recurrence rate (y-axis) and IHC4 score (x-axis) for DAB-IHC (yellow) and QIF-AQUA analysis (blue) with dashed lines representing 95% CI.

The present technology relates generally to methods for determining a risk of recurrence of disease in a cancer patient.

In a first aspect, the methods include a step of determining a level of expression of each of at least three of the following four biomarkers, including estrogen receptor (ER), progesterone receptor (PR), human epidermal growth factor receptor 2 (HER2) and Ki-67 (Ki67), in a tumor specimen taken from a cancer patient, the determination utilizing a technique that provides a continuous, quantitative score of the level of expression of each of the at least three of said four biomarkers.

Biomarker Expression

The biomarkers embodied in the present invention are known in the art, and include ER, PR, HER2 and Ki67. Estrogen receptors, in particular ERα, are expressed on certain breast tumor cells. Progesterone receptors are intracellular steroid receptors that specifically bind progesterone. The role of progesterone receptors in cancers, such as many types of breast cancer are recognized in the art. Human Epidermal Growth Factor receptor 2 (HER2) is a protein that is understood in the art to play an important role in the pathogenesis and progression of certain aggressive types of breast cancer. Antigen Ki-67 is a known nuclear protein associated with cellular proliferation.

It is understood that additional biomarkers are known in the art as relevant to cell proliferation and cancer, including breast cancer and ER and/or PR positive breast cancer. The disclosure herein in no way limits or precludes the use of additional biomarkers in the present invention.

Continuous, Quantitative Score Determination

The present invention provides methods of determining which cancer patients might have a greater or lesser risk of recurrence of disease, the first steps of which require a quantitative determination of the level of at least three biomarkers, chosen from the group including ER, PR, HER2 and Ki67. This determination may be effected using any technique capable of measuring a quantitative level of protein expression, but preferably a technique that is an objective, reproducible, quantitative, multiparametric analysis of one or more proteins in a given tumor sample.

A tumor sample for use in the present invention should be taken as an invasive tissue sample (e.g., a needle biopsy). Material other than tumor cells, such as for example, stroma or other neighboring tissue may be present in the tissue sample and may be specifically excluded from the analysis such that biomarker expression of ER, PR, HER2 and Ki67 expression is specifically quantified in the tumor cells.

The traditional means of assessing protein expression is known in the art, and includes techniques such as immunohistochemistry (IHC) techniques. Techniques for clinical testing are available in the art including for HER2 clinical testing (Wolff et al., *American Society of Clinical Oncology/College of American Pathologists Guideline Recommendations for Human Epidermal growth Factor Receptor 2 Testing in Breast Cancer*, Journal of Clinical Oncology, Vol 25 No. 1 pages 118-145, 2007); ER and PR testing (Hammond et al., *American Society of Clinical Oncology/College of American Pathologists Guideline Recommendations for Immunohistochemical testing of Estrogen and Progesterone Receptors in Breast Cancer*, Arch. Pathol. Lab. Med., 2010) and Ki67 testing (Dowsett et al., *Assessment of Ki67 in Breast Cancer Recommendations of the International Ki67 in Breast Cancer Working Group*, J Natl Cancer Inst 2011: 103:1656-1664). Quantitative analysis techniques including automated analysis towards standardization of IHC techniques are described by Cregger et al., *Immunohistochemistry and Quantitative Analysis of Protein Expression*, Arch. Pathol. Lab. Med., Vol. 130, 2006, and incorporated by reference.

Further, image analysis procedures have been developed in response to demand for a biologically accurate system of analysis, which is not provided by a simple result of positive or negative for the desired protein. Image analysis procedures are those that perform protein analysis using images obtained with the help of virtual or digital microscopy and whole-slide imaging. Apart from tissue specimen staining, image analysis procedures require an optical microscope system, an image acquisition system, software that controls the scan process, a digital slide viewer, and, optionally, an image processing system and/or a slide feeder. For a more complete description, see Rojo et al, *Critical Comparison of 31 Commercially Available Digital Slide Systems in Pathology*, International Journal of Surgical Pathology, 2006, 14:285.

For use in the present methods, high-resolution images of the tissue specimen stained for the nuclear compartment, ER, PR, HER2, Ki67 and/or epithelial cytoplasmic subcellular compartment are desired. In order to obtain a high-resolution image in the presently claimed methods, a digital camera or image generator capable of 1024/1024 pixels or greater should preferably be utilized.

There are a number of computer-based image analysis programs designed specifically for the quantitative analysis of IHC. Systems include MIRAX HistoQuant by 3D Histech (Budapest, Hungary); Aperio Image Analysis Toolbox/Spectrum™ by Aperio (Vista, Calif.); in Form™ by Caliper Life Sciences, PerkinElmer (Hopkinton, Mass.); ACIS® III by Dako (Carpinteria, Calif. and Glostrup, Denmark); Tissue Studio® by Definiens (Munchen Germany and Parsippany, N.J.); NDP.analyze by Hamamatsu (Japan); Ariol, Tissue IA2.0 by Leica (Buffalo Grove, Ill.); VIAS™ by Ventana Medical Systems (Tucson Ariz.); TissuemorphDP™ by Visiopharm (Hoersholm, Denmark) and AQUA® technology by HistoRx (Branford, Conn.). In microscopic analysis of biomarker expression in biological samples, "quantitative" has been used to refer to the number of something, e.g. the number of cells; the size of something, e.g. cell size, volume or length; or the amount of something, i.e. the amount or concentration of a biomarker. In the context of the present invention, "quantitative" refers to the measurement of the amount or the concentration (or relative concentration) of biomarker expression in the specimen. Unlike traditional IHC, the AQUA system is objective and produces strictly quantitative in situ protein expression data on a continuous scale. The AQUA system takes advantage of the multiplexing power of fluorescence by using multiple markers to molecularly differentiate cellular and sub-cellular compartments within which simultaneous quantification of biomarkers-of-interest can be performed. In addition, AQUA analysis provides for standardization and a high degree of reproducibility with % CVs less than 5%, which is superior to any chromagen-based IHC quantification system available to date (Gustayson et al., *Standardization of HER2 Immunohistochemistry in Breast Cancer by Automated Quantitative Analysis*, 2009 Arch. Path. Lab. Med. Vol 133 pages 1413-1419).

Using AQUA technology, a standardized score is produced which quantifies the level of protein expression. The system and/or software are configured to process the acquired digital images to automatically detect, localize, and quantitate measurement of protein biomarker intensity. The AQUA score is automatically determined from one or more digital images of the tissue sample, the scoring being reflective of biomarker expression level in a defined compartment and/or subcellular compartment in the tissue section. See Welsh et al., *Standardization of Estrogen Receptor Measurement in Breast Cancer Suggests False-Negative Results Are a Function of Threshold Intensity Rather Than Percentage of Positive Cells*, J. Clinical Oncology 2011; Gustayson et al., *Standardization of HER2 Immunohistochemsitry in Breast Cancer by Automated Quantitative Analysis* Arch. Path. Lab. Med. Vol 133 pg 1413-1419, 2009.

AQUA technology employs a computer-assisted method for quantifying ER, PR, HER2 and Ki67 expression within a subcellular compartment of individual cells of said population of tumor cells. Using one or several tissue sections, the tumor sample is incubated with a first stain that specifically labels a nuclear compartment (e.g. DAPI) of individual cells, a second stain specific for ER, a third stain specific for PR, a fourth stain specific for HER2, a fifth stain specific for Ki67, and a sixth stain specific for epithelial cytoplasmic (e.g. cytokeratin) subcellular compartment. Next, a high resolution image is obtained of each of the first through sixth stains retained in the tissue sample using an automated digital pathology system to provide a first image of the nuclear compartment and additional images of ER, PR, HER2, Ki67, and epithelial cytoplasmic subcellular compartment.

The images can then be analyzed as intensity based or intensity and area based. In one embodiment, the following intensity-based or intensity- and area-based analysis is conducted.

Image pixels within an area defined as tumor are analyzed to identify pixels containing tumor cell nuclear subcompartment data and those containing tumor cell non-nuclear subcompartment data, as described in Camp et al. *Automated subcellular localization and quantification of protein expression in tissue microarrays*, Nature Medicine Vol 8 No 11 2002; Gustayson et al., *Development of an unsupervised pixel-based clustering algorithm for compartmentalization of immunohistochemical expression using Automated QUantiative Analysis*, Appl Immunohistochm Morl Morphol. Vol 17 No. 4 pages 329-337, 2009. Then the pixel intensity of the biomarker staining of the pixels of the subcellular compartment of interest is analyzed to generate an score rendered by dividing the total intensity value by the total area of the compartment.

From the foregoing procedure, an objective, reproducible, quantitative, multiparametric analysis of the level of expression of each of said four biomarkers can be achieved.

Continuous marker scores were normalized prior to inclusion in the defined IHC4 Algorithm I. A scale was derived to map ER and PgR marker data from 0-10, per the IHC4 model Algorithm I. Normalization was carried out for ER/PgR as follows: (QIF-AQUA score—minimum score for cohort)/(range of QIF-AQUA scores for cohort). HER2 QIF-AQUA scores were dichotomized by binary logistic regression with the TEAM IHC/FISH clinical diagnostic results. After the cutpoint was applied, there was an overall concordance of 92.8% between QIF-AQUA HER2 data and conventional IHC/FISH data. AQUA-QIF scores for Ki67 were generated by an AQUA algorithm producing scores corresponding to the percentage of positive cells in the tumor region which were not modified. Positive Ki67 pixels were identified by thresholding using minimally Ki67 positive controls with the following calculation applied: [(Positive Ki67 Pixels/Positive Nuclear Pixels)*100]. The algorithm was validated independent of Ki67 by using ER (data not shown) against both pathologist manual read (Pseudo R2=0.77; p<0.001) and 15-year overall survival (1% cutoff; p<0.001).

Cumulative Score Based on a Score Model

The present invention provides methods of calculating a cumulative score, based on a score model. The score model can be based on an algorithm wherein the quantitative score of at least three of the biomarkers, including ER, PR, HER2 and Ki67 of a tumor specimen taken from a cancer patient are imputed into the score model to arrive at a cumulative score, which can be used to assess the risk of recurrence of disease in the patient. Although several specific algorithms are disclosed herein, it is understood that the algorithms from which the embodied score models are derived are not limited to these specific examples.

Incorporation of the continuous, quantitative scores of the biomarkers into a score model and arriving at a cumulative score can be conducted manually, or it can be incorporated into code for computer-readable instructions, such as, for example, AQUA analysis.

For the generation of new models using Cox regression, backward elimination (based on Wald statistics which corrects for multiple comparisons) was used to determine included model covariates (entrance criteria, p≤0.10). To obtain a continuous relationship between the model scoring and recurrence-free survival, constrained cubic splines were fit to the hazard function estimates for each patient resulting from the Cox modeling described above. The discriminative ability of the models was quantified using Harrell's concordance index (c-index), standard errors were obtained using bootstrapping with 1000 replications.

In one embodiment, the score model is algorithm (I), which is:

$$IHC4_{cs}=94.7*[0.100ER_{10}-0.079PR_{10}+0.586HER2+0.240 \ln(1+10*Ki67)] \quad (I)$$

in which $ER_{10}$ represents the normalized, continuous, quantitative score of the level of expression of ER; $PR_{10}$ represents the normalized continuous, quantitative score of the level of expression of PR; HER2 represents the dichotomized score from, continuous, quantitative scores for the level of expression of HER2; and Ki67 represents the percent positive, continuous, quantitative score of Ki67. Under algorithm (I), ER and PR are determined on a scale of 1-10 as a continuous, quantitative score of the level of expression, for example, by the respective AQUA score minimum over the range; HER2 represents the dichotomized, continuous, quantitative score of the level of expression of HER2; and Ki67 represents the continuous, quantitative score of the level of expression of Ki67 determined as a % of tumor nuclei positive.

In another embodiment, the score model is algorithm (II), which is:

$$IHC4_{cs}=(-0.151*ER)-(0.207*PR)+(0.217*HER2)+(0.077*Ki67) \quad (II)$$

in which ER represents the continuous, quantitative score of the level of expression of ER; PR represents the continuous, quantitative score of the level of expression of PR; HER2 represents the continuous, quantitative score of the level of expression of HER2; and Ki67 represents the continuous, quantitative score of the level of expression of Ki67.

In another embodiment, the score model is algorithm (III), which is:

$$IHC4_{cs}=(-0.151*ER)-(0.207*PR)+(0.217*HER2)+(0.077*Ki67) \quad (III)$$

in which ER represents the continuous, quantitative score of the level of expression of ER; PR represents the continuous, quantitative score of the level of expression of PR; HER2 represents the dichotomous score, derived from the continuous, quantitative score of the level of expression of HER2; and Ki67 represents the continuous, quantitative score of the level of expression of Ki67.

In another embodiment, the score model may be derived i.e. algorithm (A), which is:

$$IHC4_{cs}=(A*ER)+(B*PR)+(C*HER2)+(D*Ki67) \quad (A)$$

in which ER represents the continuous, quantitative score of the level of expression of ER; PR represents the continuous, quantitative score of the level of expression of PR; HER2 represents the continuous, quantitative score of the level of expression of HER2; Ki67 represents the continuous, quantitative score of the level of expression of Ki67; and A, B, C and D are numerical coefficients determined from Cox proportional hazard regression models used for univariate and multivariate models in which analysis is performed using recurrence-free survival (RFS) or disease-free survival (DFS) at, for example, 8 years from the analysis of a relevant patient cohort. Once derived, Algorithm A would be validated in a prospective analysis of an independent cohort.

The cumulative score derived from the score model can be used to quantify a risk of recurrence of disease in a cancer patient. Determining the risk of recurrence of a patient can be determined based on the patient's cumulative score from quantitative analysis, manifested by a score taken from a continuous scale, as imputed to a score model. Predetermined reference scores are garnered from a cohort of cancer patients. In an embodiment, the scores are garnered from ER positive tumor cohort.

The cumulative score derived from the score model is an independent predictor of outcome when clinical prognostic factors are included in multivariate regression analyses. In one embodiment, the regression of IHC4 by AQUA scores against recurrence free survival (RFS) showed a continuous positive correlation between increasing scores and increasing recurrence rate. The model can remain a significant predictor of outcome regardless of treatment (e.g., exemestane vs. tamoxifen).

Figure 2:
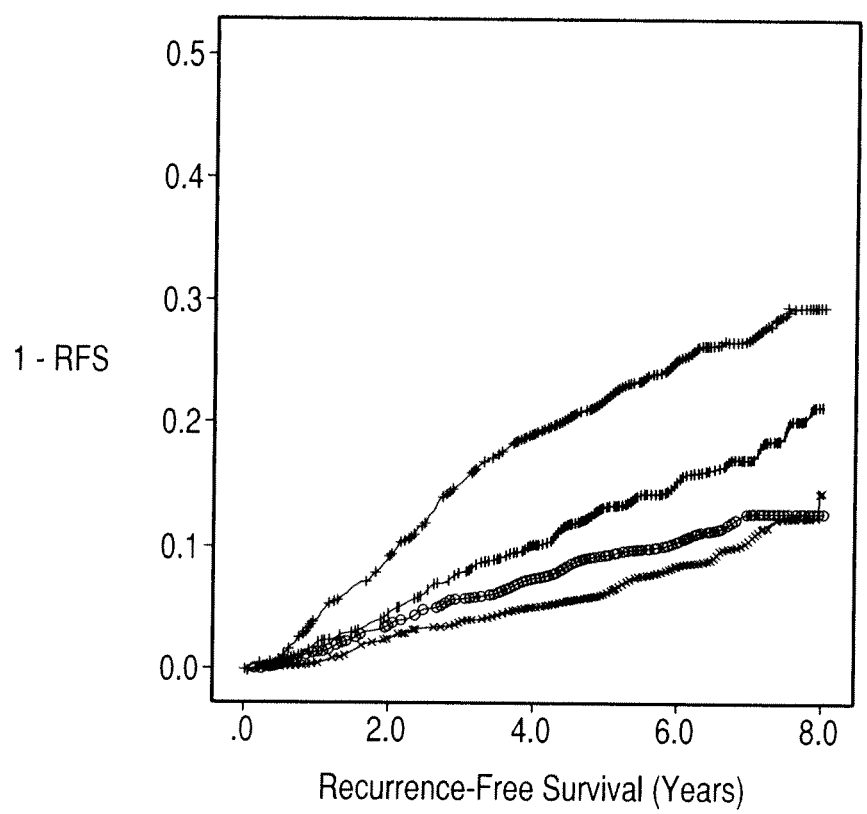
FIG. 2 illustrates an embodiment of the Recurrence Free Survival Prediction calculated using traditional IHC analysis scores from tumor specimens from the TEAM trial. Quartiles are shown as: the first quartile (blue, bottom line); second quartile (green, second to bottom line); third quartile (beige, third from bottom line) and fourth quartile (purple, top line). The first and second quartiles do not demonstrate a statistically significant variation.
Figure 3:
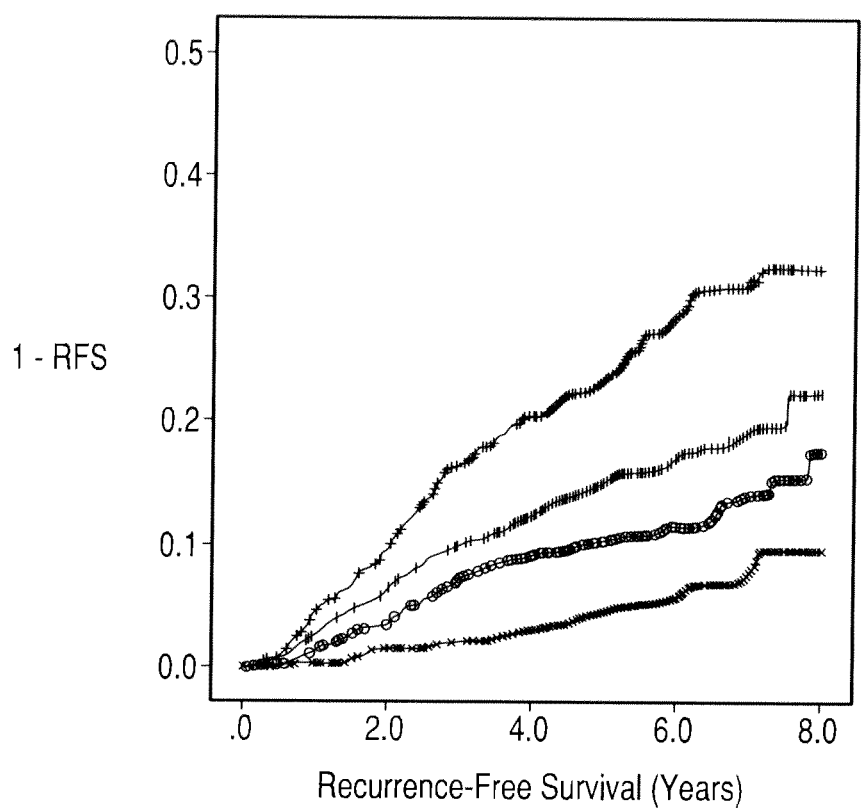
FIG. 3 illustrates an embodiment of the Recurrence Free Survival Prediction by IHC4 by AQUA analysis using the Algorithm I, Cuzick model Algorithm I. Cumulative incidence curve plots showing the recurrence relationship between IHC4 scores broken into indicated quartiles QIF-AQUA analysis Quartiles are shown as: the first quartile (blue, bottom line); second quartile (green, second to bottom line); third quartile (beige, third from bottom line) and fourth quartile (purple, top line). The first and second quartiles demonstrate a statistically significant variation.
Figure 4:
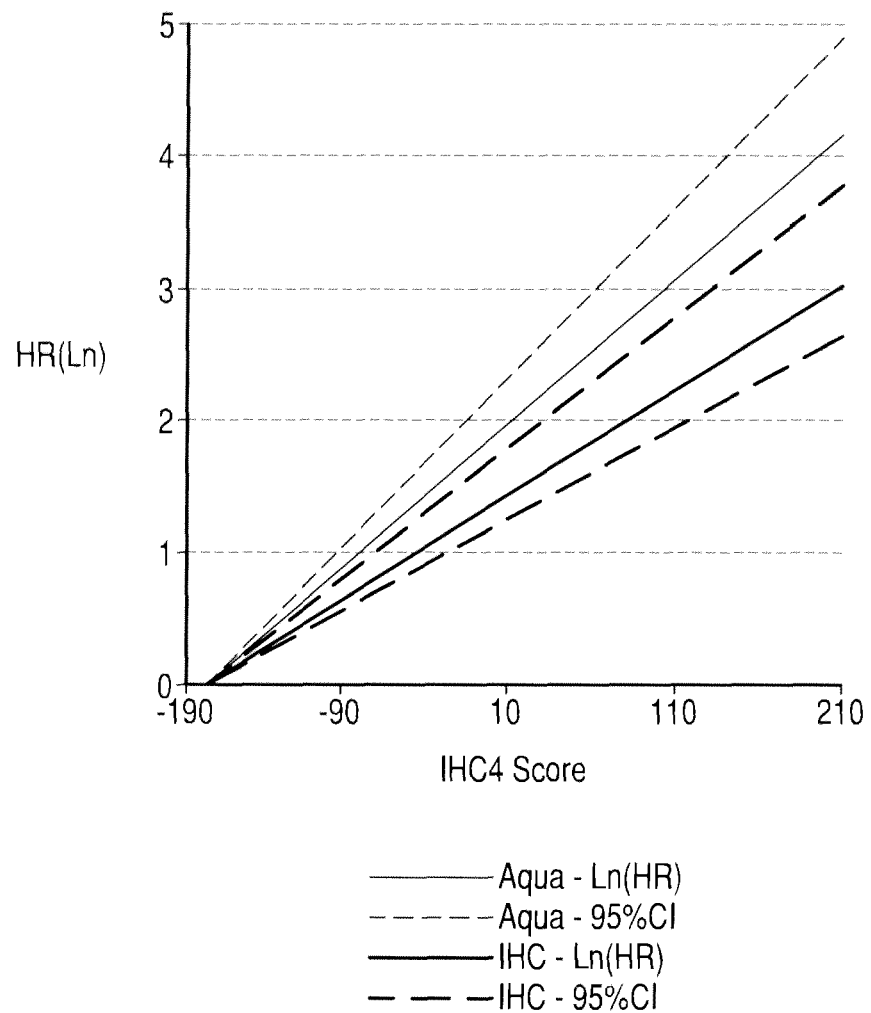
FIG. 4 illustrates an embodiment of the regression of Hazard ratio and recurrence rate comparisons for DAB-IHC and QIF-AQUA in Algorithm I scoring models. Regression plot demonstrating relationship between the natural log of the hazard ratio (HR(ln); y-axis) and IHC4 score (X-axis) for both DAB-IHC-based (red) and QIF-AQUA-based (blue) Cox modeling with dashed lines representing 95% CI of the HR.
Figure 5:
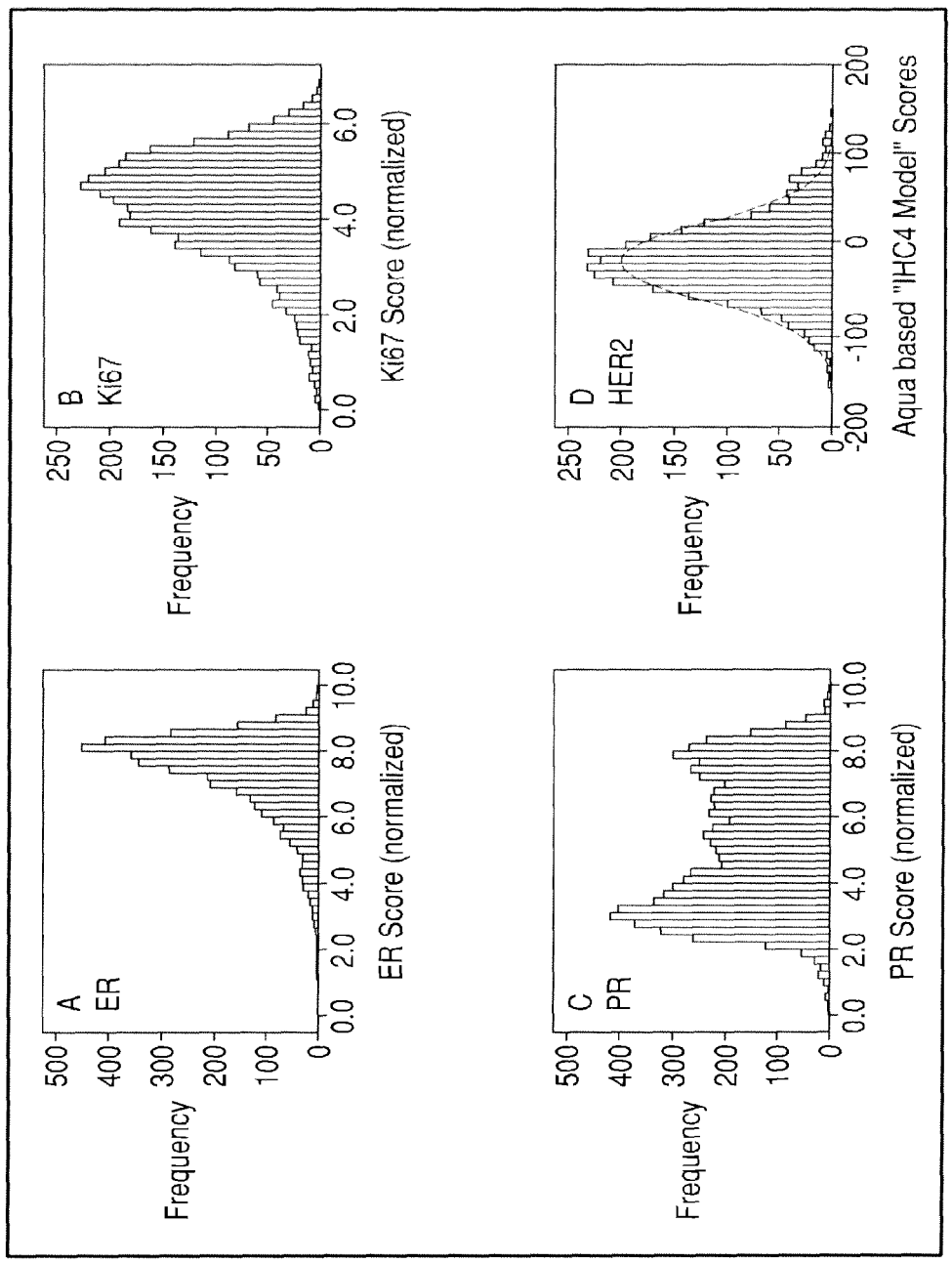
FIG. 5 illustrates an embodiment of Histogram distribution of QIF-AQUA-based expression scores for ER (A), Ki67(B), PR(C), and HER2 (D) in the TEAM cohort.

In another embodiment, the scores for a cohort of patients can be separated into statistically significant risk groups or segments that quantify varying levels of risk of recurrence of disease. These risk groups can then be used to predict recurrence and/or survival of a patient. In one embodiment, the scores for a cohort can be broken up into segments, for example, quartiles, wherein the quartiles are statistically significant in quantifying levels of risk of recurrence of disease. For example, the first and second quartiles can provide statistically significant in quantification of risk of recurrence of disease. As used herein, the first quartile indicates the lowest risk of recurrence of disease and the fourth quartile indicates the highest risk of recurrence of disease, as shown in examples embodied in FIGS. 2-4. Based on the quartile or segment in which a patient's cumulative score falls, a care taker can develop an appropriate treatment regimen in light of the risk of recurrence of disease.

Once established for a given technique, a predetermined reference score, for example a cumulative score derived from the score model, can be used for comparison with any patient's risk score derived from the level of ER, PR, HER2 and/or Ki67 expression determined in a tumor specimen from the patient, using a standardized platform. In consultation with physicians, additional factors may be weighted in determining the reference value for each platform.

Expected Benefits

The methods of the present invention, in some embodiments, further comprise a step of selecting the cancer patient whose score falls within a predetermined reference score. In one embodiment, the cancer patient's score demonstrates an increased likelihood of recurrence of disease (e.g., a patient assigned to the fourth quartile reference score), and is one who will likely benefit from a treatment regimen, preferably an aggressive treatment regimen, including chemotherapy, radiation therapy, or a combination thereof. Likewise, in another embodiment, the cancer patient's score demonstrates a decreased likelihood of recurrence of disease (e.g., a patient assigned to the first quartile reference score), and is one who would not be expected to benefit from a treatment regimen, even an aggressive one, including chemotherapy, radiation therapy, or a combination thereof. Also, the cancer patient who is assigned to the intermediate quartiles is considered a candidate with intermediate risk, and may benefit from additional treatment or supervision from a doctor or other medical professional.

The methods of the present invention, in some embodiments, further comprise prescribing a treatment regimen to a patient determined to be at a high risk of recurrence of disease, preferably an aggressive treatment regimen. Aggressive treatments are known and practiced in the art. For example, in some embodiments, the present invention may include subjecting a patient determined to be at a high risk of recurrence of disease to radiation therapy and/or subjecting a patient determined to be at a high risk of recurrence of disease to chemotherapy and/or other aggressive form of treatment known in the art.

Kits

Additional aspects of the present invention provide for kits to be used in patient treatment for determining a risk of recurrence of disease in a cancer patient comprising reagents for determining a continuous, quantitative score of a level of expression, if desired, of each of four biomarkers, including ER, PR, HER2 and Ki67, in a tumor specimen taken from a cancer patient. In an embodiment, the kits also contain instructions for the use of said reagents, assay methods, calculation of risk score from assay results, and/or interpretation of risk score.

The kits may contain several specific reagents, including for example, stains specific for the nuclear compartment of the cells and each of the biomarkers. In one embodiment, the kit reagents include a first stain specific for a nuclear compartment of a cell; a second stain specific for ER; a third stain specific for PR; a fourth stain specific for HER2; a fifth stain specific for Ki67; and a sixth stain specific for epithelial cytoplasmic subcellular compartment. In another embodiment, the kit reagents include a first stain specific for a nuclear compartment of a cell; a second stain specific for epithelial cytoplasmic subcellular compartment; and at least three additional stains that are each specific for one of four biomarkers, including ER, PR, HER2 and Ki67.

Suitable stains for use in the kits of the present invention include but are not limited to: Anti estrogen receptor antibodies such as 1D5, PharmDx (1D5 and ER-2-123), 6F11, ER88, SP1; anti progesterone receptor antibodies such as Clone PgR636, 1294, 1A6, 312; anti HER2 antibodies such as A0485 (Dako, Carpinteria, Calif.), CB11 (Ventana, Tuscon, Ariz.), 4D5; anti-Ki67 antibodies SP6 (Biocare Medical, Concord, Calif.) MIB1; nuclear stain DAPI; non-nuclear epithelial cytoplasmic antibody pan-cytokeratin; Fluorophores that may be conjugated to a primary antibody include but are not limited to Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, Fluor X, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)amino]caproyl] (NBD), BODIPY™, boron dipyrromethene difluoride, Oregon Green, MITOTRACKER™ Red, DiOC.sub.7 (3), DiIC.sub.18, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Lissamine, Umbelliferone, Tyrosine and Tryptophan. Wide varieties of other fluorescent probes are available commercially.

Further amplification of the signal can be achieved by using combinations of specific binding members, such as antibodies and anti-antibodies, where the anti-antibodies bind to a conserved region of the target antibody probe, particularly where the antibodies are from different species. Alternatively specific binding ligand-receptor pairs, such as biotin-streptavidin, may be used, where the primary antibody is conjugated to one member of the pair and the other member is labeled with a detectable probe. Thus, one effectively builds a sandwich of binding members, where the first binding member binds to the cellular component and serves to provide for secondary binding, where the secondary binding member may or may not include a label, which may further provide for tertiary binding where the tertiary binding member will provide a label.

The secondary antibody may be labeled using avidin, strepavidin or biotin, which are each independently labeled with a detectable moiety, such as a fluorescent dye (stain), a luminescent dye or a non-fluorescent dye. In principle, an enzyme that (i) can be conjugated to or bind indirectly to (e.g., via conjugated avidin, strepavidin, biotin, secondary antibody) a primary antibody, could be used. The enzyme employed can be, for example, alkaline phosphatase, horseradish peroxidase, beta-galactosidase and/or glucose oxidase. The enzyme can also be directed at catalyzing a luminescence reaction of a substrate, such as, but not limited to, luciferase and aequorin, having a substantially non-soluble reaction product capable of luminescencing or of directing a second reaction of a second substrate, such as but not limited to, luciferine and ATP or coelenterazine and Ca.sup.++, having a luminescencing product.

In a preferred embodiment the antibodies used in QIF-AQUA analysis are ER (1D5, 1:100), PgR (Clone PgR636, 1:500), HER2 (A0485, 1:8000; all Dako, Carpinteria, Calif.), and Ki67 (SP6, 1:1000, Biocare Medical, Concord, Calif.) and the algorithm is Algorithm I or II. In other embodiments alternative antibodies may be used in conjunction with an algorithm derived as taught herein.

Computer System

In one embodiment, the method of the present invention is implemented by a computer system including one or more computers. In one embodiment, the computer system includes one or more excitation light sources, optical components, image capture components, storage components and one or more processors, configured to execute a computer program comprising computer-readable instructions for determining a continuous, quantitative score of a level of expression of each of at least three of the following four biomarkers, including estrogen receptor (ER), progesterone receptor (PR), human epidermal growth factor receptor 2 (HER2) and Ki-67 (Ki67), in a tumor specimen taken from a cancer patient; determining a cumulative score based on a score model that incorporates said at least three continuous, cumulative scores; and determining a risk of recurrence of disease in the cancer patient based on the cumulative score. In an embodiment, the level of expression of each of at least three of the four biomarkers is quantified reproducibly.

Non-Transitory Computer-Usable Medium

In another embodiment, the present invention is directed to a non-transitory computer-usable medium having computer-readable instructions stored thereon for execution by a processor to perform a method for determining a continuous, quantitative score of a level of expression of each of at least three of the following four biomarkers, including estrogen receptor (ER), progesterone receptor (PR), human epidermal growth factor receptor 2 (HER2) and Ki-67 (Ki67), in a tumor specimen taken from a cancer patient.

In yet another embodiment, the present invention is directed to a non-transitory computer-usable medium having computer-readable instructions stored thereon for execution by a processor to perform a method for determining a continuous, quantitative score of a level of expression of each of at least three of the following four biomarkers, including estrogen receptor (ER), progesterone receptor (PR), human epidermal growth factor receptor 2 (HER2) and Ki-67 (Ki67), in a tumor specimen taken from a cancer patient; determining a cumulative score based on a score model that incorporates said at least three continuous, quantitative scores; and determining a risk of recurrence of disease in the cancer patient based on the cumulative score.

In another embodiment, the invention is directed to a non-transitory computer-usable medium having program code recorded thereon that, when executed on a computing system, automatically processes immunofluorescence data, the program code comprising: code for processing a digital microscopy image of a stained tumor specimen taken from a cancer patient to extract data related to intensity values associated with one or more stains; code for processing the extracted data to arrive at a value for intensity per pixel for each of the one or more stains; code for processing pixel intensity of at least one stain for determining pixels associated with a preselected subcompartment and determining the area of the subcompartment for use as a denominator; code for processing pixel intensity of a second stain for determining an expression level of a biomarker on a continuous scale and a value for total biomarker intensity in the same preselected subcompartment for use as a numerator; code for calculating from the numerator and denominator a quantitative score of the biomarker expression per area; optionally, code for processing the total area (pixels) stained by Ki67 as the numerator; optionally, code for total tumor nuclear compartment area as the denominator; code for collecting the quantitative score of each of at least three of the following four biomarkers, including estrogen receptor (ER), progesterone receptor (PR), human epidermal growth factor receptor 2 (HER2) and Ki-67 (Ki67); and optionally code for incorporating the continuous, quantitative scores of the at least three biomarkers into a score model for arriving at a cumulative score. The non-transitory computer-usable medium having program code recorded thereon can further comprise code for determining a risk of recurrence of disease in the cancer patient based on the cumulative score. The non-transitory computer-usable medium having program code recorded thereon can further comprise code for assigning the cumulative score to first, second, third, or fourth quartile. The non-transitory computer-usable medium having program code recorded thereon can further comprise code for determining a risk of recurrence of disease in the cancer patient based on the cumulative score by designating the position of the cumulative score of the patient on a curve of possible scores from a population of patients.

Providing a Recurrence Risk Score

In another embodiment, the present invention is directed to a method of providing a recurrence risk score. This method may be carried out by someone other than a treating physician, such as for example, a diagnostic laboratory. In one embodiment, the method of determining a risk of recurrence score in a cancer patient comprises: determining a level of expression of each of at least three of the following four biomarkers, including estrogen receptor (ER), progesterone receptor (PR), human epidermal growth factor receptor 2 (HER2) and Ki-67 (Ki67), in a tumor specimen taken from a cancer patient, the determination utilizing a technique that provides a continuous, quantitative score of the level of expression of each of the at least three of said four biomarkers; and determining a cumulative score based on a score model in which the continuous, quantitative scores provided by the technique, one each for the at least three of said four biomarkers, are incorporated. In some embodiments the continuous, quantitative score is intensity-based, or both intensity-based and area-based. In other embodiments, the continuous, quantitative score is determined for each of said four biomarkers. The technique, in an embodiment, includes an automated, quantitative image analysis procedure or the technique includes an automated, quantitative, immunofluorescence image analysis procedure, and the automated, quantitative image analysis procedure may be implemented by an automated, digital pathology system or a immunofluorescence pathology system.

EXAMPLES

Example 1: Clinical Cohort

The cohort used to study and develop IHC4 models with AQUA technology was the Tamoxifen Exemestane Adjuvant Multinational Phase III ("TEAM clinical trial") (Camp et. al., *Automated subcellular localization and quantification of protein expression in tissue microarrays*. Nat. Med. 2002; 8(11):1323-1327; Dolled-Filhart et. al., *Quantitative in situ cancer proteomics: molecular pathology comes of age with automated tissue microarray analysis*. Personal Med. 2005; 2(4):291-300.) a multinational, open-label study in postmenopausal patients with early ER/PgR-positive invasive breast cancer who had completed primary therapy. The co-primary endpoints were disease-free survival at 2.75, and 5 years defined as the time from randomization to the earliest documentation of disease relapse (locoregional or distant primary tumor recurrence, ipsilateral or contralateral breast cancer, or mortality from any cause). Pathology blocks for approximately 4800 cases in the pathology cohort were received at a central laboratory and replicate tissue microarrays (TMA) constructed according to current guidelines (Faratian et. al., *Rapid screening of tissue microarrays for Her-2 fluorescence in situ hybridization testing is an accurate, efficient and economic method of providing an entirely in situ hybridization-based Her-2 testing service*, Histopathology. 2009; 54(4):428-432.18). TMAs were then analyzed by conventional IHC (DAB-IHC) analyzed using quantitative image analysis (Giltnane et al. *Technology insight: Identification of biomarkers with tissue microarray technology*. Nat Clin Pract Oncol. 2004; 1(2):104-111.19) and QIF using AQUA technology.

Traditional IHC:

Conventional Immunohistochemistry (DAB-IHC) staining was performed centrally at the University of Edinburgh as previously described. Antibodies used were ER (Clone 6F11, 1:50 dilution, Novocastra™, Newcastle, UK), PgR (Clone PgR636, 1:50 dilution), HER2 and Ki67 (Herceptest), (Clone MIB1, 1:50 dilution, all Dako Cambridge UK). A single batch of antibody and reagents was used to perform all assays, incubations were temperature controlled. Replicate tissue microarrays were analyzed for ER(n=6), PgR (n=6), HER2(n=3), and Ki67(n=3) staining.

Quantitative Immunofluorescence Analysis:

QIF-AQUA analysis using fluorescent immunohistochemical staining was carried centrally out at HistoRx, Inc. (Branford, Conn., USA) as described previously for epithelial-based tumors (Camp 2002; Gustayson et al 2009). Antibodies used in QIF-AQUA analysis were ER (1D5, 1:100), PgR (Clone PgR636, 1:500), HER2 (A0485, 1:8000; all Dako, Carpinteria, Calif.), and Ki67 (SP6, 1:1000, Biocare Medical, Concord, Calif.). For HER2 QIF-AQUA scores were assessed in the epithelial tumor membrane/cytoplasmic compartment, defined by cytokeratin immunoreactivity and exclusion of the nuclear compartment, and nuclear compartment, defined by tumor-specific DAPI reactivity and exclusion of membrane/cytoplasmic compartment, for ER/PgR/Ki67. Quantitative biomarker expression was calculated from the Cy5 fluorescent signal intensity within each image pixel. The AQUA-QIF score was generated as previously described from the analysis of triplicate tissue microarrays [Gustayson et al 2009 Appl Immunohistochem Mol Morphol 17:329-337]. AQUA-QIF scores for Ki67 were generated by an AQUA algorithm producing scores corresponding to the percentage of positive cells in the tumor region which were not modified. Positive Ki67 pixels were identified by thresholding using minimally Ki67 positive controls with the following calculation applied: [(Positive Ki67 Pixels/Positive Nuclear Pixels)*100]. The algorithm was validated independent of Ki67 by using ER against both pathologist manual read (Pseudo $R2=0.77$; $p<0.001$) and 15-year overall survival (1% cutoff; $p<0.001$).

Statistical Analysis

The IHC4 modelAlgorithm I utilized a linear combination of multiple markers (ER, PR, HER2, and Ki67) derived from adjusted scores generated by standard immunohistochemical scoring methods. Continuous marker scores were normalized prior to inclusion in the defined IHC4 model (1). For DAB-IHC scores: ER Histoscores were divided by 30, PgR % positive cells were divided by ten, Ki67 scores, represented as % positive cells, were included in the model without modification. HER2 was treated as a dichotomous variable (0=negative/1=positive) based upon current clinical guidelines for IHC and FISH reflex scoring (22, 23). For QIF-AQUA scores, a scale was derived to map ER and PgR marker data from 0-10, per the IHC4 model. Normalization was carried out for ER/PgR as follows: (QIF-AQUA score–minimum score for cohort)/(range of QIF-AQUA scores for cohort). HER2 QIF-AQUA scores were dichotomized by binary logistic regression with the TEAM IHC/FISH clinical diagnostic results (data not shown). After the cutpoint was applied, there was an overall concordance of 92.8% between QIF-AQUA HER2 data and conventional IHC/FISH data (data not shown). QIF-AQUA scores for Ki67 were generated with an algorithm to count % positive cells and scores included in the model without modification.

All analyses were conducted using SPSS statistical software version 15.0 or later (SPSS Inc, Chicago, Ill.). Cox proportional hazard regression models were used to assess all univariate and multivariate models described in the text. All analyses were performed using 8-year recurrence-free-survival (RFS) or disease-free survival (DFS). Additional clinical variables used, when specified, in analyses were patient age (continuous variable), tumor size in mm (continuous variable), nodal status (N-stage, categorical variable), and histologic grade (categorical variable).

Summary of Methods for Determining IHC4 Score Utilizing AQUA Scores and Algorithm 1

For the generation of new models using Cox regression, backward elimination (based on Wald statistics) was used to determine included model covariates (entrance criteria, p≤0.10). To obtain a continuous relationship between the model scoring and recurrence-free survival, constrained cubic splines were fit to the hazard function estimates for each patient resulting from the Cox modeling described above (1). The discriminative ability of the models was quantified using Harrell's concordance index (c-index)(34), standard errors were obtained using bootstrapping with 1000 replications.

Results:

Distributions of each AQUA marker after normalization were similar to the three IHC normalized markers (ER, PR, Ki67; FIG. 1). Normalized variables were then put into the following algorithm to calculate the "IHC4" score (1) previously described:

$$94.7*(-0.100*ER10-0.079*PgR10+0.586*Her20/1+0.240*Ln(1+10*Ki67\% \text{ pos})).$$

Distribution of IHC4 scores using AQUA scores in Algorithm I had a mean=−3.9. IHC4 scores were analyzed as continuous covariates in separate univariate Cox regression models. The Cox regression model was highly significant (P<0.0001) with the AQUA IHC4 model showing a higher (non-overlapping 95% CI) HR of 1.011 (95% CI: 1.010-1.013) and the model was a highly significant (P<0.0001) independent predictors of outcome when other recognized clinical prognostic factors (histologic grade, tumor size, age, N staging) were included in multivariate regression analyses. Additionally, regressing AQUA IHC4 model against recurrence rate, using cubic spline regression curve fitting, showed a continuous positive correlation between increasing scores and increasing recurrence rate.

Furthermore, there was no effect or interaction between treatment group and the model with the model remaining a significant predictor of outcome regardless of treatment (exemestane vs. tamoxifen). There was no significant interaction between the model and chemotherapy, indicating the IHC4 model is an independent prognostic predictors of outcome.

To further illustrate the relationship between the model and recurrence-free survival in the TEAM trial cohort, the individual scoring distributions were divided into quartiles and plotted as cumulative incidence curves. The quartiles maintained rank. In an exploratory sub-set analysis the separation of the bottom quartile (0-25%) from the next highest quartile (26%-50%) is significant for the AQUA IHC4 model (p=0.004) but not for the DAB-IHC IHC4 model (p=0.110) using Cox proportional Hazards modeling.

New Algorithm Discovery Using the TEAM Cohort:

In addition to transforming scores to utilize the Cuzick IHC4 Algorithm I, we performed de novo Cox regression modeling for the four prognostic markers using the raw data to derive new models based QIF-AQUA independently of the Cuzick-based IHC4 transformation/normalization. A new algorithm with overall p-values <0.0001 for Cox proportional hazards modeling using continuous covariates were developed. For QIF-AQUA score new model (log 2-transformed), all four markers entered the model at the 10% level, although the HER2 component had borderline significance p=0.074 in the final model. Individual patient scores were generated for the new model using the derived coefficients shown in Table 2. Correlation of the IHC4-based and de novo model was 0.88 (Spearman). When entered into a Cox proportional hazards regression, the de novo model was highly significant for prediction of outcome (p<0.001; Table 3) and independent of clinical factors (histologic grade, tumor size, age, N staging; Table 3).

Example 3: AQUA Scores Used in the IHC4 Model of Algorithm 2

An IHC4 model was next developed utilizing the continuous AQUA scores for ER, PR, HER2, and Ki67 and the TEAM trial clinical data.

TABLE 2

Methods for Developing IHC4 model of Algorithm 2

| Marker | Coefficient^ | Hazard Ratio (95% CI) | P-value* |
|---|---|---|---|
| ER | −0.151 | 0.86 (0.80-0.93) | <0.001 |
| PR | −0.207 | 0.81 (0.77-0.86) | <0.001 |
| HER2 | 0.217 | 1.24 (1.14-1.35) | <0.001 |
| Ki67 | 0.077 | 1.08 (0.99-1.18) | 0.074 |

*Model criteria P value at 0.01 for inclusion in test
^Based on AQUA scores (log2 transform)

TABLE 3

Predictor of Recurrence, Independent of Clinical Variables for IHC4 model of Algorithm 2

| Parameter | n (%) | Hazard Ratio (95% CI) | P-Value |
|---|---|---|---|
| Marker Data Only | | | |
| Model(Continuous) | 2917 (100) | 2.72 (2.30-3.21) | <0.001 |
| Model w/Clinical Features | | | |
| Model(Continuous) | 2727 (100) | 2.88 (1.99-2.86) | <0.001 |
| Histological Grade | | | |
| I | 294 (11) | | |
| II | 1432 (52) | 1.73 (1.10-2.73) | 0.018 |
| III | 1003 (37) | 2.22 (1.40-3.54) | 0.001 |
| Size (continuous) | 2727 (100) | 1.02 (1.01-1.02) | <0.001 |
| Age (continuous) | 2727 (100) | 1.01 (1.00-1.02) | 0.044 |
| N-Staging | | | |
| Pos | 1111 (41) | | |
| Neg | 1618 (59) | 1.86 (1.50-2.31) | <0.001 |

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein.

The above-described embodiments can be implemented using hardware, software, or a combination thereof. When implemented in software, the software code can be executed on any suitable processor or collection of processors, whether provided in a single-computer system or distributed among multiple computers.

Further, it should be appreciated that a computer may be embodied in any of a number of forms, such as a rack-mounted computer, a desktop computer, a laptop computer, a server computer, a cloud-based computing environment, a tablet computer, a special-purpose computer, etc. Additionally, a computer may be embedded in a device not generally regarded as a computer but with suitable processing capabilities, including a Personal Digital Assistant (PDA), a smart phone or any other suitable portable or fixed electronic device.

Various embodiments may include hardware devices, as well as program products comprising computer-readable ("computer-usable"), non-transient storage media for carrying or having data or data structures stored thereon for carrying out processes as described herein. Such non-transient media may be any available media that can be accessed by, for instance, a general-purpose or special-purpose computer. By way of example, such non-transient storage media may comprise random-access memory (RAM), read-only memory (ROM), erasable programmable read-only memory (EPROM), electrically-erasable programmable read-only memory (EEPROM), field-programmable gate array (FPGA), flash memory, compact disk, or other optical disk storage, magnetic disk storage or other magnetic storage devices, or any other medium which can be used to carry or store desired program code in the form of computer-executable instructions or data structures and which can be accessed by a general-purpose or special-purpose computer. Combinations of the above may also be included within the scope of non-transient storage media. Volatile computer memory, non-volatile computer memory, and combinations of volatile and non-volatile computer memory may also be included within the scope of non-transient storage media. Computer-executable instructions may comprise, for example, instructions and data that cause a general-purpose computer or special-purpose computer to perform a certain function or group of functions.

In addition to a system, various embodiments are described in the general context of methods and/or processes, which may be implemented in some embodiments by a program product including computer-executable instructions, such as program code. These instructions may be executed by computers in networked or in non-networked environments. The terms "method" and "process" are synonymous unless otherwise noted. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

In some embodiments, the method(s) and/or system(s) discussed throughout may be operated in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet. Those skilled in the art will appreciate that such network computing environments may encompass many types of computer system configurations, including personal computers, hand-held devices, multi-processor systems, microprocessor-based or programmable consumer electronics, network PCs, minicomputers, mainframe computers, and the like.

In some embodiments, the method(s) and/or system(s) discussed throughout may be operated in distributed computing environments in which tasks are performed by local and remote processing devices that may be linked (such as by hardwired links, wireless links, or by a combination of hardwired or wireless links) through a communications network. In a distributed computing environment, according to some embodiments, program modules may be located in both local and remote memory storage devices. Data may be stored either in repositories and synchronized with a central warehouse optimized for queries and/or for reporting, or stored centrally in a database (e.g., dual use database) and/or the like.

The various methods or processes outlined herein may be coded and executable on one or more processors that employ any one of a variety of operating systems or platforms.

Embodiments of the computing system can include a processing unit characterized by anyone of the following component configurations: logic circuits that respond to and process instructions fetched from the main memory unit; a microprocessor, a processor, a microcontroller, a processing unit with a single processing core, a processing unit with two processing cores, a processing unit with more than one processing cores or any other combination of logic circuits capable of executing the systems and methods described herein.

Additionally, such software may be written using any of a number of suitable programming languages and/or programming or scripting tools, and also may be compiled as executable machine language code or intermediate code that is executed on a framework or virtual machine. The computer-executable code may include code from any suitable computer programming or scripting language or may be compiled from any suitable computer-programming language, such as, but not limited to, ActionScript, C, C++, C#, Go, HTML, Java, JavaScript, JavaScript Flash, Objective-C, Pert, PHP, Python, Visual Basic, and XML.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer-usable medium or media can be transportable, such that the program or programs stored thereon can be loaded onto one or more different computers or other processors to implement various aspects of the present invention as discussed above. The recitation of a module, logic, unit, or circuit configured to perform a function includes discrete electronic and/or programmed microprocessor portions configured to carry out the functions. For example, different modules or unit that perform functions may be embodied as portions of memory and/or a microprocessor programmed to perform the functions.

Additionally, it should be appreciated that according to one aspect, one or more computer programs that, when executed, perform methods of the present invention, need not reside on a single computer or processor, but may be distributed in a modular fashion amongst a number of different computers or processors to implement various aspects of the present invention.

While specific embodiments have been disclosed, the various embodiments are not to be considered limiting. One of ordinary skill in the art will understand that variations and modifications flow from the teachings provided herein.

What is claimed is:

1. A method of treating a patient that has been diagnosed with breast cancer, the method comprising the steps of:
(A) determining whether the patient is at risk of recurrence of cancer by:
obtaining or having obtained a tumor specimen from the patient;
performing or having performed an expression assay on the tumor sample to calculate a cumulative score based on a score model incorporating a level of expression of each of the following four biomarkers, including estrogen receptor (ER), progesterone receptor (PR), human epidermal growth factor receptor 2 (HER2) and Ki-67 (Ki67), wherein said step utilizes a technique that provides a quantitative score on a continuous scale of the level of expression of each of said four biomarkers;

assigning the patient based on the cumulative score to a first, second, third or fourth quartile of a cohort, the first quartile representing cancer patients having lowest cumulative scores and lowest risk of recurrence of disease and the fourth quartile representing cancer patients having highest cumulative scores and highest risk of recurrence of disease;

and (B) if the patient is in the second, third or fourth quartile, then administering an aggressive treatment regimen to the patient, wherein the aggressive treatment regimen comprises chemotherapy, radiotherapy, or a combination thereof.

2. The method of claim 1 in which the aggressive treatment regimen comprises radiation therapy.

3. The method of claim 1 in which the aggressive treatment regimen comprises chemotherapy.

4. The method of claim 1 in which the quantitative score on a continuous scale is intensity-based.

5. The method of claim 1 in which the quantitative score on a continuous scale is both intensity-based and area-based.

6. The method of claim 1 in which the patient is ER positive.

7. The method of claim 6 in which the patient has undergone anti-estrogen hormonal treatment.

8. The method of claim 1 in which the patient has yet to undergo treatment for the patient's breast cancer.

9. The method of claim 1 in which the aggressive treatment regimen is administered to the patient only if the patient is in the fourth quartile.

10. The method of claim 1 in which the patient assigned to the first quartile is considered a candidate who would not be expected to benefit from a treatment regimen selected from chemotherapy, radiation therapy, and a combination thereof.

11. The method of claim 1 in which the patient assigned to the second or third quartile is considered a candidate with intermediate risk, and may benefit from additional treatment or supervision.

12. The method of claim 1 in which the technique includes an automated, quantitative image analysis procedure.

13. The method of claim 1 in which the technique includes an automated, quantitative, immunofluorescence image analysis procedure.

14. The method of claim 12 in which the automated, quantitative image analysis procedure is implemented by an automated, digital pathology system.

15. The method of claim 12 in which the automated, quantitative image analysis procedure is implemented by an automated, digital, immunofluorescence pathology system.

16. The method of claim 1 in which the score model that provides the cumulative score ($IHC4_{cs}$) comprises an algorithm (I), which is:

$$IHC4_{cs}=94.7*[0.100ER_{10}-0.079PR_{10}+0.586HER2+0.240\ln(1+10*Ki67)] \quad (I)$$

in which $ER_{10}$ represents the normalized, quantitative score on a continuous scale of the level of expression of ER;

$PR_{10}$ represents the normalized quantitative score on a continuous scale of the level of expression of PR;

HER2 represents the dichotomized score from, quantitative scores on a continuous scale for the level of expression of HER2; and Ki67 represents the percent positive score of Ki67.

17. The method of claim 1 in which the score model that provides the cumulative score ($IHC4_{cs}$) comprises an algorithm (II), which is:

$$IHC4_{cs}=(-0.152*ER)-(0.007*PR)+(0.001*HER2)+(0.082*Ki67) \quad (II)$$

in which

ER represents the quantitative score on a continuous scale of the level of expression of ER;

PR represents the quantitative score on a continuous scale of the level of expression of PR;

HER2 represents the quantitative score on a continuous scale of the level of expression of HER2; and Ki67 represents the quantitative score on a continuous scale of the level of expression of Ki67.

18. The method of claim 1 in which the score model that provides the cumulative score ($IHC4_{cs}$) comprises an algorithm (III), which is:

$$IHC4_{cs}=(-0.151*ER)-(0.207*PR)+(0.217*HER2)+(0.077*Ki67) \quad (III)$$

in which

ER represents the quantitative score on a continuous scale of the level of expression of ER;

PR represents the quantitative score on a continuous scale of the level of expression of PR;

HER2 represents the dichotomous score, derived from the quantitative score on a continuous scale of the level of expression of HER2; and Ki67 represents the continuous, quantitative score of the level of expression of Ki67.

19. The method of claim 18 in which the technique includes a reproducible, quantitative, multiparametric analysis of the level of expression of each of said four biomarkers.

20. A method of treating a cancer patient comprising:

administering a treatment regimen selected from chemotherapy, radiation therapy, and a combination thereof to a cancer patient based on high risk of recurrence of disease, in which (i) the risk of recurrence of disease is based on a cumulative score that incorporates quantitative scores on a continuous scale of a level of expression of each of the following four biomarkers, estrogen receptor (ER), progesterone (PR), human epidermal growth factor receptor 2 (HER2), and Ki-67 (Ki67) in a tumor specimen from said cancer patient, and (ii) the cancer patient has been assigned to a second, third or fourth quartile of a cohort based on the cumulative score, the fourth quartile representing cancer patients having highest cumulative scores and highest risk of recurrence of disease, wherein the cancer patient has been diagnosed with breast cancer.

21. The method of claim 20 in which the cancer patient has been assigned to the fourth quartile of the cohort based on the cumulative score.

* * * * *